United States Patent
Libbey et al.

(10) Patent No.: US 9,995,761 B2
(45) Date of Patent: Jun. 12, 2018

(54) METHOD FOR SIMULTANEOUS OBSERVATION OF THREE DEGREES OF VIBRATIONAL FREEDOM USING SINGLE HETERODYNE BEAM

(71) Applicant: The United States of America, as represented by the Secretary of the Army, Washingtion, DC (US)

(72) Inventors: Bradley W. Libbey, Alexandria, VA (US); James D. Perea, Alexandria, VA (US)

(73) Assignee: THE UNITED STATES OF AMERICA, AS REPRESENTED BY THE SECRETARY OF THE ARMY, Washington, DC (US)

( * ) Notice: Subject to any disclaimer, the term of this patent is extended or adjusted under 35 U.S.C. 154(b) by 0 days. days.

(21) Appl. No.: 15/485,261

(22) Filed: Apr. 12, 2017

(65) Prior Publication Data

US 2017/0285063 A1    Oct. 5, 2017

Related U.S. Application Data

(62) Division of application No. 15/088,201, filed on Apr. 1, 2016, now Pat. No. 9,651,477.

(51) Int. Cl.
*G01B 9/02* (2006.01)
*G01P 3/36* (2006.01)

(52) U.S. Cl.
CPC ..................................... *G01P 3/36* (2013.01)

(58) Field of Classification Search
CPC .................. G01P 3/36; G01N 21/1702; G01N 2201/0683; G01N 2201/12; G01N 2201/06113; G01N 2201/06; G01H 9/00
See application file for complete search history.

(56) References Cited

U.S. PATENT DOCUMENTS

| | | | |
|---|---|---|---|
| 4,018,531 A | 4/1977 | Leendertz | |
| 4,834,111 A | 5/1989 | Khanna et al. | |
| 4,913,547 A | 4/1990 | Moran | |
| 5,011,280 A | 4/1991 | Hung | |
| 6,008,887 A | 12/1999 | Klein et al. | |

(Continued)

OTHER PUBLICATIONS

P. Hariharan, Basics of Interferometry, Academic Press, pp. 201-202, published 2007.

(Continued)

*Primary Examiner* — Hwa Lee
(74) *Attorney, Agent, or Firm* — Richard J. Kim (57) ABSTRACT

A laboratory system has demonstrated the measurement of three degrees of vibrational freedom simultaneously using a single beam through heterodyne speckle imaging. The random interference pattern generated by the illumination of a rough surface with coherent light can be exploited to extract information about the surface motion. The optical speckle pattern is heterodyne mixed with a coherent reference. The recorded optical data is then processed to extract three dimensions of surface motion. Axial velocity is measured by demodulating the received time-varying intensity of high amplitude pixels. Tilt, a gradient of surface velocity, is calculated by measuring speckle translation following reconstruction of the speckle pattern from the mixed signal.

10 Claims, 4 Drawing Sheets

(56) References Cited

U.S. PATENT DOCUMENTS

| | | | |
|---|---|---|---|
| 7,193,720 B2 * | 3/2007 | Gatt | G01H 9/00 356/489 |
| 7,242,481 B2 | 7/2007 | Shpantzer et al. | |
| 7,812,965 B2 | 10/2010 | Hill | |
| 2005/0228838 A1 | 10/2005 | Stetson et al. | |
| 2005/0237533 A1 * | 10/2005 | Lal | G01H 9/00 356/486 |
| 2008/0144041 A1 * | 6/2008 | Muenter | G01H 9/00 356/484 |

OTHER PUBLICATIONS

P. Jacquot and J.M. Fournier, Interferometry in Speckle Light: Theory and Applications, Springer, pp. 51-58, published 2000.
H. J. Tiziani, "Analysis of Mechanical Oscillations by Speckling," Applied Optics, vol. 11, No. 12, pp. 2911-2917, published 1972.
R. Jones and C. Wykes, "Holographic and Speckle Interferometry," Cambridge University Press, pp. 122-125, published 1983.
J. W. Goodman, "Introduction to Fourier Optics", Roberts and Company Publishers, pp. 66-68 & 74-75, published 2005.
B.K. Park, O. Boric-Lubecke, and V.M. Lubecke, "Arctangent demodulation with DC offset compensation in quadrature Doppler radar receiver systems," IEEE Trans. Microw. Theory Tech., vol. 55, No. 5, pp. 1073-1079, published May 2007.

* cited by examiner

METHOD FOR SIMULTANEOUS OBSERVATION OF THREE DEGREES OF VIBRATIONAL FREEDOM USING SINGLE HETERODYNE BEAM

REFERENCE TO RELATED APPLICATIONS

This is a divisional patent application of copending application Ser. No. 15/088,201 filed Apr. 1, 2016, entitled "Method and Apparatus for Simultaneous Observation of Three-Degrees of Vibrational Freedom Using Single Heterodyne Beam." The aforementioned application is hereby incorporated herein by reference.

GOVERNMENT INTEREST

The invention described herein may be manufactured, used, sold, imported, and/or licensed by or for the Government of the United States of America.

FIELD OF THE INVENTION

The present invention relates to coherent optical vibration sensing, specifically for observation of three-degrees of freedom using temporal heterodyne speckle imaging.

STATEMENT REGARDING PRIOR DISCLOSURES BY THE CO-INVENTORS

An article co-authored by James Perea and Brad Libbey, (the co-inventors), entitled, "Development of a heterodyne speckle imager to measure 3-degrees of vibrational freedom," was submitted to The Optical Society earlier in 2016 for publication in an Optical Express publication in 2016, the publication date TBD.

BACKGROUND OF THE INVENTION

Coherent optical vibration sensors have been investigated for use in numerous applications including strain measurements, equipment diagnostics, medical imaging, and seismic sensing. Various techniques are utilized to observe surface motion. These techniques include, but are not limited to heterodyne laser Doppler vibrometry (e.g., U.S. Pat. No. 4,834,111 A Khanna et al.) for observation of surface velocity in the axial dimension of the interrogation beam, shearography (e.g., U.S. Pat. No. 5,011,280 A Hung) for observation of the gradient of displacement in two dimensions, electronic speckle pattern interferometry (e.g., U.S. Pat. No. 4,018,531 A Leendertz) for in-plane or out of plane displacement or out of plane displacement gradients, and speckle pattern imaging for out of plane displacements. The techniques listed are generally used for observation of one or two degrees of freedom. Variations using multiple coherent beams (e.g., U.S. Pat. No. 7,242,481 B2 Shpantzer et al.) have been used to observe three degrees of freedom.

It is of interest to simultaneously observe three-degrees of freedom using a single coherent beam.

The current invention combines elements of heterodyne Doppler vibrometry and digital speckle photography along with signal processing routines to simultaneously observe velocity in the axial dimension of the interrogation beam and out of plane tilts of the illuminated region. This provides the ability to observe three-degrees of freedom using a single coherent beam.

SUMMARY OF THE INVENTION

The disclosure relates to measuring the motion of a surface plane by imaging optical speckle that has been modulated by a heterodyne process. A process takes the sequence of heterodyne images and extracts motion with three degrees of freedom. The device takes advantage of a probing optical field that illuminates the rough surface. The spatial optical field is described based on previous work. (See, e.g., P. Hariharan, Basics of Interferometry, Academic Press, 2007; P. Jacquot and J. M. Fournier, Interferometry in Speckle Light: Theory and Applications, Springer, 2000; H. J. Tiziani, "Analysis of Mechanical Oscillations by Speckling," Applied Optics, vol. 11, no. 12, pp. 2911-2917, 1972; and R. Jones and C. Wykes, "Holographic and Speckle Interferometry," Cambridge University Press, 1983.) These models are typically independent of time, but this invention takes advantage of surface motion that affects the probe beam by causing a phase shift due to path length change over time. The invention adds an optical frequency shift to observe these phase and amplitude shifts creating a heterodyne system.

The moving surface alters the path length of a probe beam in time. To aid in understanding this invention, it is useful to define the geometry of this moving surface. This surface is described in a $\{\xi,\eta,z\}$ coordinate system, where $\xi$ and $\eta$ are in the surface plane and z is orthogonal to the plane. The sensor can determine two types of motion; out of plane pistoning in the axial direction z, and tilting of the plane in two directions. Out of plane motion results in a Doppler phase shift and tilting results in a translation of the speckle image. (See, e.g., R. Jones and C. Wykes, "Holographic and Speckle Interferometry," Cambridge University Press, 1983, incorporated herein by reference.) A single dimension of tilting $\theta$ is presented to simplify illustration, however, the addition of a second tilting degree-of-freedom $\phi$ parallels the picture below and is superimposed in the section detailing the invention. The moving surface has a pivot point that is allowed to translate in the z direction, but is otherwise located at a fixed position $\xi=\xi_0$. The position of a scattering point $P_1$, originally on the z=0 plane at $\{\xi,0,0\}$, will be moved to a new location $P_2$, FIG. 1. This motion extends the path length of reflected light; the path length is used to determine the speckle image resulting from these two locations in a method paralleling Tiziani. (See, e.g., H. J. Tiziani, "Analysis of Mechanical Oscillations by Speckling," Applied Optics, vol. 11, no. 12, pp. 2911-2917, 1972, incorporated herein by reference.)

In one aspect, an exemplary heterodyne speckle imaging sensor system is disclosed. In another aspect, an exemplary method for simultaneous observation of three-degrees of vibrational freedom is disclosed based on a heterodyne speckle imaging sensor system.

Finally, an exemplary signal processing method is disclosed for computing three-degrees of vibrational freedom using a heterodyne beam. Such a signal processing method comprises the steps of accessing a complete measurement of temporal spatial irradiance data obtained using a heterodyne beam as stored as pixel frames of image data on a computer; high-pass filtering each pixel independently to isolate heterodyne signal from the complete measurement to output heterodyne information at a local oscillator frequency; applying a computation process for sequential estimates of a detected probe speckle pattern amplitude to compute two dimensions of tilt based on time sequences; applying a parallel demodulation process based on an arctangent demodulation for Doppler shifted heterodyne signals applied to each pixel to calculate z-axis velocity; and displaying a representation of the computed tilt based on time sequences and the calculated z-axis velocity on a data display device.

BRIEF DESCRIPTION OF THE DRAWINGS

Additional advantages and features will become apparent as the subject invention becomes better understood by reference to the following detailed description when considered in conjunction with the accompanying drawings wherein.

DETAILED DESCRIPTION

Before entering into the detailed description of one embodiment of the present invention according to the accompanying Figures, the theory of the present invention will be explained hereinafter.

Figure 1:
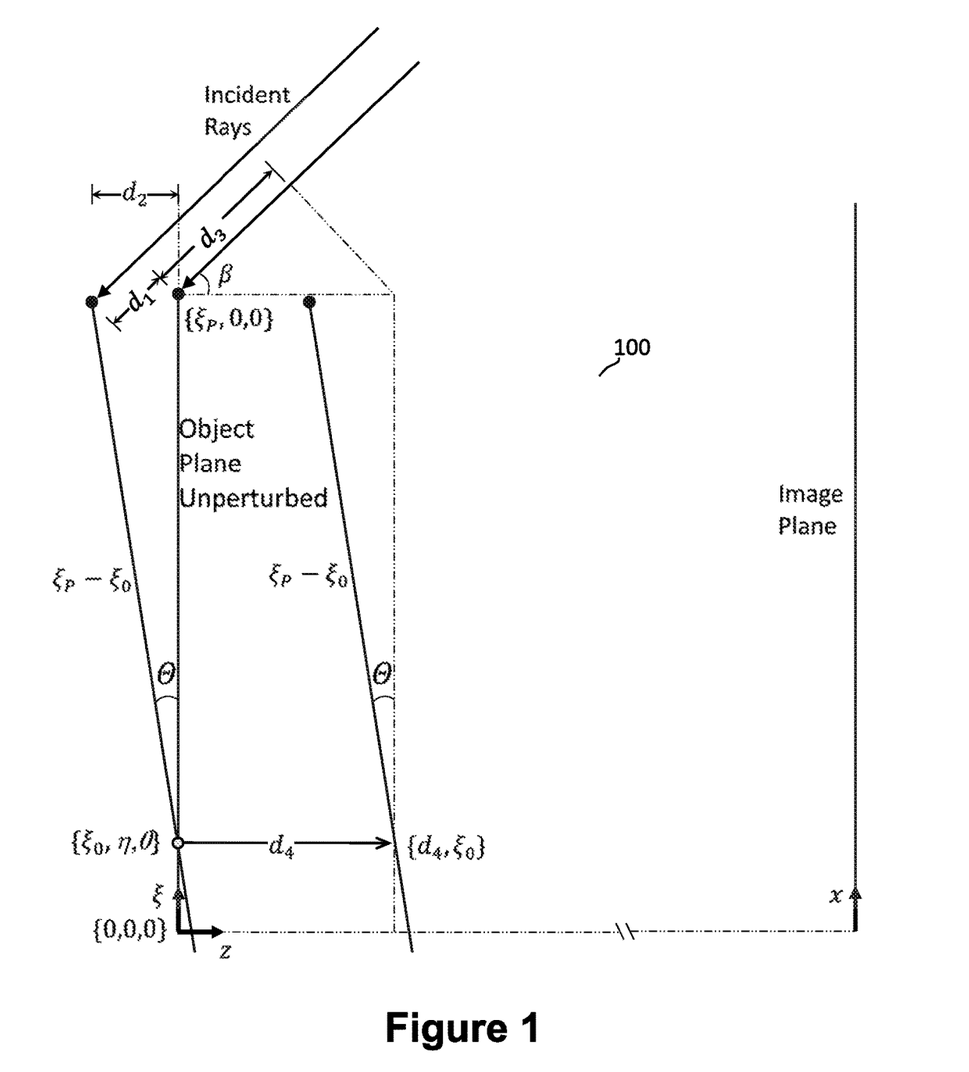
FIG. 1 shows an exemplary incident beam and moving surface geometry used to describe the three-dimensional vibration sensing method.

FIG. 1 shows an exemplary incident beam and moving surface geometry 100 used to describe the three-dimensional vibration sensing method. The object plane, z=0, is allowed to rotate about a pivot $\{\xi_0, \eta, 0\}$ and translate along the z-axis. An incident electromagnetic beam contacts $\{\xi_P, 0, 0\}$ at angle β before tilting. As the object plane rotates by angle θ, the incident electromagnetic beam impinges on a new spatial location, located distance $d_1$ away along the axis of the beam. The image plane is located a sufficient distance from the object plane to be considered in the far field.

The variation in path length ΔP due to tilt and translation is a combination of the incoming and outgoing light. The incoming light is assumed to be coherent and planar at an angle β relative to the surface plane. The image plane is assumed to be sufficiently far such that outgoing light is orthogonal to the surface plane. The path variation is geometrically determined, $$\Delta P = d_1 + d_2 - d_3 - d_4$$

$$\Delta P = (\xi - \xi_0)[\sin(\beta)(1 - \cos(\theta)) + (1 + \cos(\beta))\sin(\theta)] - d_4(1 + \cos(\beta))$$

where θ is angular change due to the tilting surface to which a small angle assumption is applied $$\sin(\theta) \cong \theta, \cos(\theta) \cong 1 - \frac{\theta^2}{2},$$

and $\theta^2 \ll \theta$. This assumption leads to a simplified path length.

$$\Delta P \approx (\xi - \xi_0)\theta(1 + \cos(\beta)) - d_4(1 + \cos(\beta))$$

In the description below the direction of illumination, and hence the Doppler velocity, are assumed to be aligned with the z-axis, β=0.

$$\Delta P \approx (\xi - \xi_0) 2 \sin(\theta) - 2d_4$$

If we maintained the cos(β) term through the subsequent equations, the velocity would be measured along an axis that is acute with the plane. This increases the utility of the method to horizontal translation as well as pistoning.

DETAILED DESCRIPTION OF THE INVENTION

Figure 2:
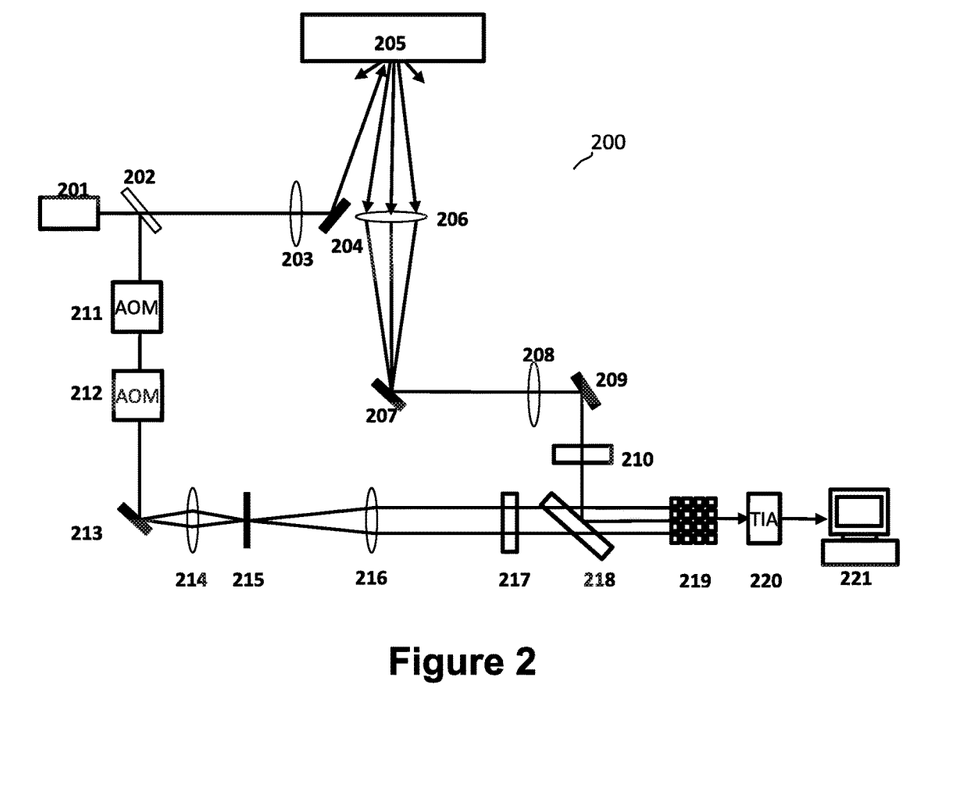
FIG. 2 shows an exemplary heterodyne speckle imaging sensor system with a dynamic diffuse-scatterer for the target.

An exemplary heterodyne speckle imaging system is represented in FIG. 2. Such an exemplary heterodyne speckle imaging sensor system 200 is shown comprising a laser source 201; a beam splitter 202; 750 mm bi-convex lens 203; a first mirror 204; a dynamic diffuse scatterer 205; 500 mm bi-convex lens 206; a second mirror 207; 250 mm plano-convex lens 208; a third mirror 209; a polarizing filter 210; a first acousto-optic modulator AOM1 211, 80.01 MHz upshift; a second acousto-optic modulator AOM2 (212), 80 MHz downshift; a fourth mirror 213; 50 mm plano-convex lens 214; 50 µm diameter spatial filter 215; 250 mm plano-convex lens 216; another polarizing filter 217; another beam splitter 218; 64×64 pixel detector 219; a trans impedance amplifier 220 sampling at 30 kHz; and a signal processor and data display 221.

Figure 3:
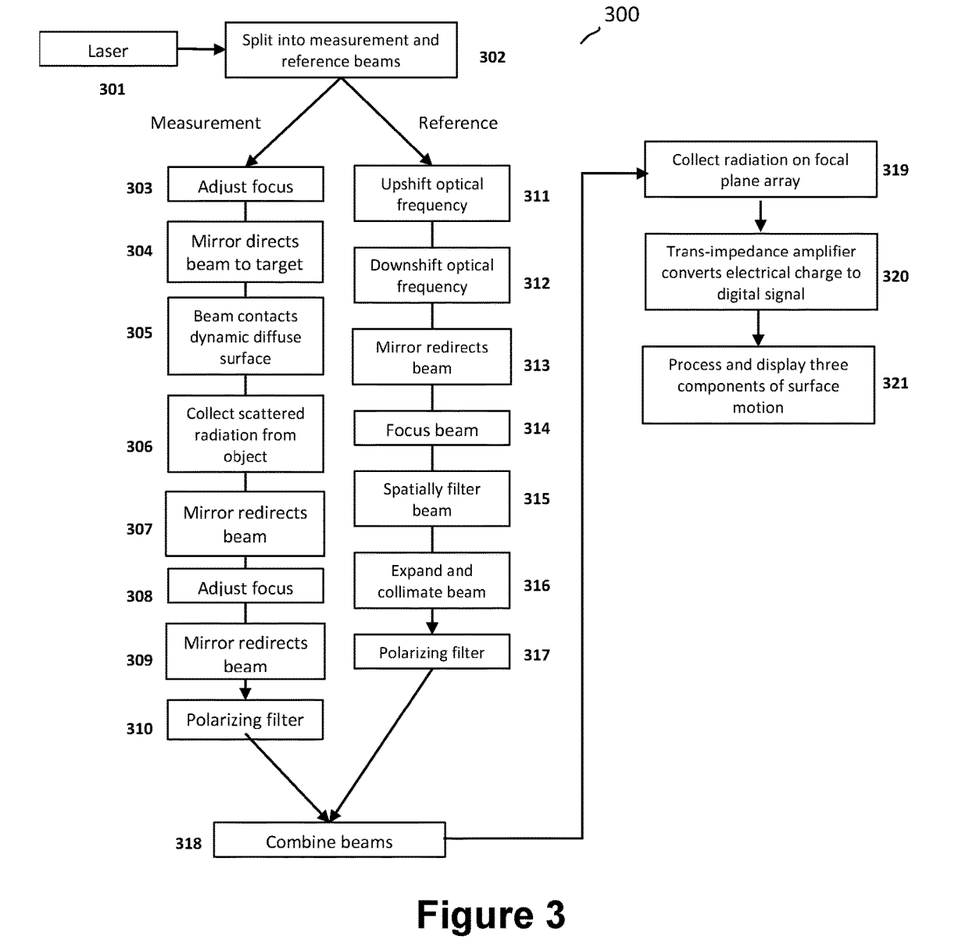
FIG. 3 shows an exemplary method for simultaneous observation of three-degrees of vibrational freedom using a heterodyne beam, e.g., of a heterodyne speckle imaging sensor system shown in FIG. 2.

FIG. 3 shows an exemplary method for simultaneous observation of three-degrees of vibrational freedom 300 using a heterodyne beam, e.g., of a heterodyne speckle imaging sensor system shown in FIG. 2. Referring now to FIGS. 2 and 3, the source 201 is a linearly polarized laser 301. A splitter 202 divides the source into a probe and reference beams 302. In the probe beam path, a single lens provides focus adjustment for 303 the beam 203 and mirror 204 redirects the beam to a dynamic object 205; the object has a diffuse surface. The electric field scatters 305 from the moving object 205 and now has a random spatial phase or amplitude. The purpose of the invention is to determine changes to the surface's position by tracking changes in the random, scattered electric field. As the object is tilted and translated, a phase shift is imparted due to the optical path change near the object plane 205. Thus, the optical field at the object is modified by a phase associated with the new position of the object.

$$u_o(\xi, \eta) \rightarrow u_o(\xi, \eta) e^{\frac{j2\pi\Delta P}{\lambda}} \quad (1)$$

Where λ is the optical wavelength.

Some of the resulting scattered radiation is collected 306 by a single lens 206. The radiation is redirected 307 using a mirror 207 and propagates through a secondary optic 208 which defocuses 308 the field relative to the image plane 219. An additional mirror 209 redirects the beam 309 through a dichroic polarizing filter 210 where the horizontally polarized radiation is absorbed 310. The radiation from the probe beam propagates to a second beam splitter 218 where half the radiation propagates through the splitter and half is redirected towards the focal plane array 219. The probe-leg electric field at the image plane 219 can be described as $U_P(x, y, t_1)$, at one time, and $U_P(x, y, t_2)$ at a later time. Where $U_P(x, y, t_2)$ is a phase modified version of $U_P(x, y, t_1)$, the field at a previous frame. The relationship between the these fields is $$U_P(x, y, t_2) = e^{\frac{j4\pi(\theta\xi_0 + d_4)}{\lambda}} e^{-j2kx\theta} e^{j2kz\phi^2} U_P(x - 2\theta z, y - 2\phi z, t_1) \quad (2)$$

Where k is the optical wavenumber. The invention makes use of this shifted and phase modified version of the original field to determine the object's motion; the spatial shift corresponds to tilting of the surface 205 while the phase corresponds to the axial motion of the surface 205.

Following initial propagation through the beam splitter 202, the reference beam propagates through two acousto-optic modulators AOM1 (211) and AOM2 (212). AOM1 211 upshifts the frequency of the electromagnetic field 311 by a specified amount AOM2 212 downshift the frequency 312 by an amount less than the upshift producing a modest frequency offset of the reference field. A mirror 213 redirects the reference beam 313 where it propagates through a focusing lens 214 to focus the beam 314. An aperture 215 is placed at the focal point of 214, acting as a spatial filter to spatial filter the beam 315. The diverging beam propagates to another lens 216 which collimates the expanded beam 316. The resulting electromagnetic radiation propagates through a dichroic polarizing filter 217 where the horizontally polarized radiation is absorbed 317. The reference field propagates to the beam splitter 218 where half the radiation transmits through the splitter.

The device uses the same propagation distance, the distance between splitter mirror 202 and beam splitter 218, on both probe and reference fields. The beam splitter 218 additively combines the probe and reference electric fields 318 in the region between splitter 218 and the focal plane array 219. The total field $U_t$ at the image plane is the superposition of the probe and reference fields.

$$U_t(x,y,t)=U_r(x,y,t)+U_p(x,y,t) \quad (3)$$

The focal plane array 219 transduces the irradiance of these two fields 319 into an electrical charge proportional to the irradiance.

$$I(x, y, t) = U_t U_t^* = U_r U_r^* + U_m U_m^* + U_r U_m^* + U_r^* U_m \quad (4)$$

$$I(x, y, t) = \frac{1}{\lambda^2 z^2}\left[R^2 + |P|^2 + 2R|P|\cos\left(\omega_{LO}t + \frac{4\pi}{\lambda}(\theta(t)\xi_0 + \phi(t)\eta_0 + d_4(t)) - \alpha_p\right)\right] \quad (5)$$

Where R and |P| are the magnitudes of the reference and probe field respectively. The combined irradiance is the sum of three terms: 1) irradiance of the reference $R^2$, 2) irradiance of the probe $|P|^2$ and 3) the mix term R|P|.

The system relies on a heterodyne component where the reference field strength amplifies the probe field. This is possible since the reference field is frequency shifted at a frequency equal to $\omega_{LO}$, the difference frequency of AOM1 211 and AOM2 212. The magnitude 2R|P| of the heterodyne irradiance shifts spatially in direct proportion to the surface tilt 205. The phase terms associated with $\cos(\omega_{LO}t+\psi)$ contain sufficient information to compute the z-axis velocity of the surface. This phase term modulates the local oscillator frequency, $\omega_{LO}$. The phase is $$\psi(t) = \frac{4\pi}{\lambda}(\theta(t)\xi_o + \phi(t)\eta_o + d_4(t)) - \alpha_p \quad (6)$$

where the term containing $d_4$ is the Doppler shift due to translation of the object in the z dimension. The terms containing $\theta$ and $\phi$ are Doppler shift due to the tilting motion. It occurs in this expression because the pivots do not intersect the origin and the illumination is assumed to be centered at the origin. In other words, this term represents motion in the z direction based on the amount of tilt and the relative distance between the pivot point and the center of illumination. The two terms just described do not depend on spatial position on the image plane. In contrast $\alpha_p(x,y)$ is the phase of the probe speckle pattern and will shift in a manner similar to the magnitude of the speckle pattern.

A trans-impedance amplifier circuit 220 converts charge from the focal plane array 219 into a digital representation 320 of the irradiance on a computer 221. The acquisition is repeated sequentially in time at a frame rate sufficient to observe the intermediate carrier frequency resulting from the upshift and downshift from the acousto-optic modulators 211 and 212. The focal plane array also has sufficient pixels to observe speckles caused by light reflected from a diffuse target.

The sequence of image frames captured on the computer 221 undergoes a process on the same computer 321 to calculate tilt in the x and y directions, $\Delta\theta$ and $\Delta\phi$ respectively, as well as axial velocity in the z direction. The process is outlined in FIG. 4, with two process sequences.

Figure 4:
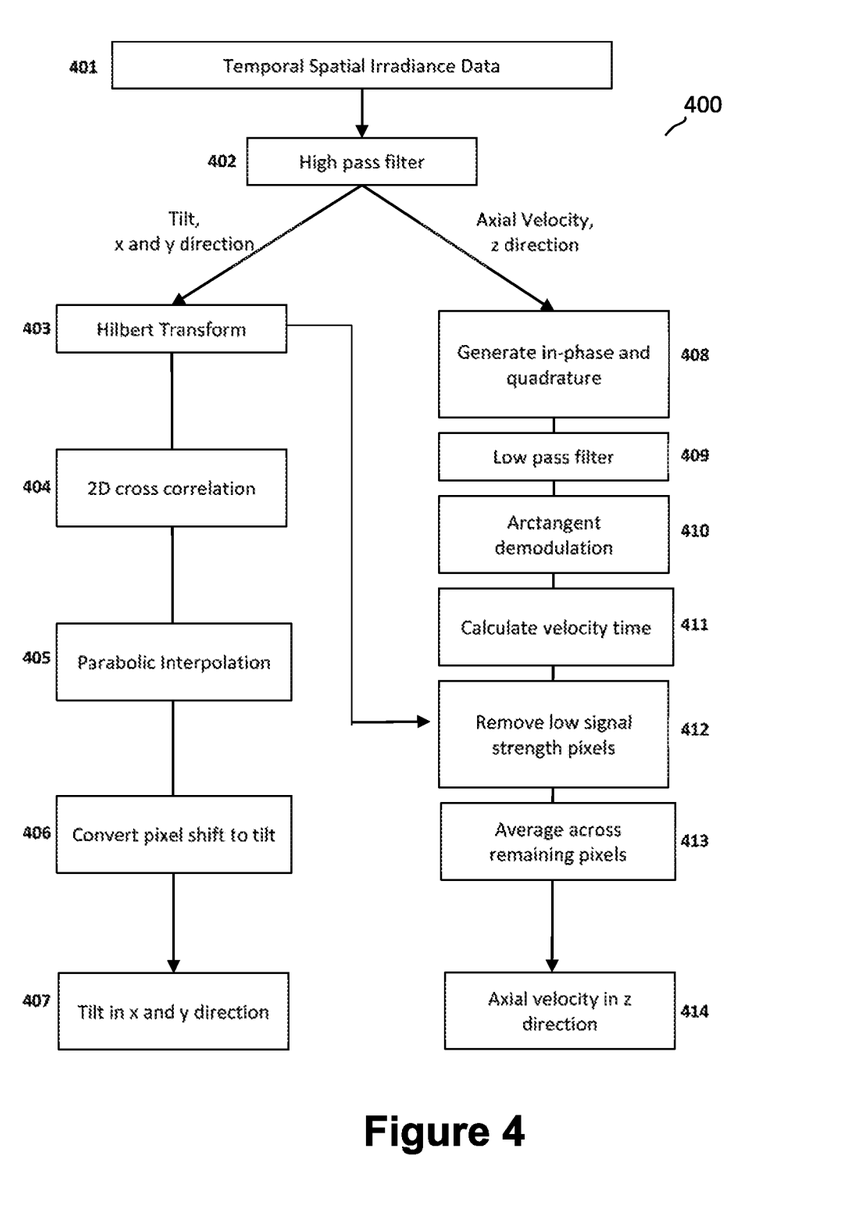
FIG. 4 shows an exemplary process for signal processing a sensor observation of three-degrees of vibrational freedom using a heterodyne beam as exemplified in FIG. 3.

FIG. 4 shows an exemplary process 400 for signal processing a sensor observation of three-degrees of vibrational freedom using a heterodyne beam. The process to produce two dimensions of tilt is based on sequential estimates of the probe leg's speckle pattern amplitude. First, the image data stored on the computer 221 is accessed 401. The heterodyne signal is isolated from the complete measurement by high-pass filtering 402 each pixel independently. This filter removes $R^2$ and $|P|^2$ from the camera's representation of the optical field, equation 5. The filter 402 outputs the heterodyne information at the local oscillator frequency $\omega_{LO}$. A temporal Hilbert transform 403 extracts the envelope 2R|P| at each pixel. The output of 403 is a speckle pattern that shifts spatially for each subsequent frame. Each frame is cross-correlated 404 with its prior time frame producing a sequence of new data frames each containing a spatial peak. A peak's position relative to center of the frame corresponds to the number of pixels shifted between two image frames. A peak's location is estimated using a two dimensional parabolic spatial fit 405 on a cross correlation frame. In this way the peak location can capture sub-pixel shifts in the image pairs and consequently small amplitudes of tilt. The output of the parabolic fit 405 is a temporal sequence of peak locations applied in two dimensions, in other words, two temporal sequences of spatial shifts $s_x$ and $s_y$ between subsequent image frames. The spatial shifts are converted 406 to units of object tilt difference $\Delta\theta$ and $\Delta\phi$ between subsequent image frames, $$\Delta\theta=s_x/2z \quad (7a)$$

$$\Delta\phi=s_y/2z. \quad (7b)$$

The tilt can then be displayed as two time sequences on a data display device 407.

A parallel sequence of the processing is used to calculate z-axis velocity. This demodulation process uses a standard arctangent demodulation for Doppler shifted heterodyne signals applied to each pixel. (See, e.g., B. K. Park, O. Boric-Lubecke, and V. M. Lubecke, "Arctangent demodulation with DC offset compensation in quadrature Doppler radar receiver systems," IEEE Trans. Microw. Theory Tech., vol. 55, no. 5, pp. 1073-1079, May 2007, incorporated herein by reference.) The output of filter 402 provides the heterodyne information at the local oscillator frequency $\omega_{LO}$ necessary to begin the demodulation. In-phase and quadrature 408 are calculated by multiplying each pixel by the sine and cosine of the local oscillator frequency $\omega_{LO}$. The resulting in-phase $I_{demod}$ and quadrature $Q_{demod}$ time sequences are low pass filtered 409 to remove unwanted components at frequencies greater than $\omega_{LO}$.

$$Q_{demod}(t) = LP[HP[I(t)] \sin(\omega_{LO} t)] \qquad (8)$$

$$I_{demod}(t) = LP[HP[I(t)] \cos(\omega_{LO} t)] \qquad (9)$$

The in-phase and quadrature terms are then processed in block 410 that contains mathematical equation 10 and produces an estimate of the Doppler phase $\psi$ at each pixel $$\psi \approx \text{unwrap}\left[\tan^{-1}\left(\frac{Q_{demod}(t)}{I_{demod}(t)}\right)\right]. \qquad (10)$$

The velocity for each pixel is then estimated 411 using the Doppler phase.

$$v = \frac{\lambda}{4\pi}\left(\frac{\psi_2 - \psi_1}{t_2 - t_1}\right). \qquad (11)$$

The optical component 208 produces defocused images, as a result, estimates of velocity at each pixel should be equal. However, destructive interference from the diffuse scattering source 205 produces some low amplitude field strengths from the probe that are not accurately captured with the camera 219 and 220. The velocity estimates associated with low amplitude pixels will not produce accurate estimates of velocity. Process step 412 removes low signal strength pixels. The remaining pixels are averaged 413 to reduce noise. The output is displayed 414 as a single velocity time series representing axial velocity in the z direction.

It is obvious that many modifications and variations of the present invention are possible in light of the above teachings. It is therefore to be understood that within the scope of the appended claims, the invention may be practiced otherwise than as described.

What is claimed is:

1. A signal processing method for computing three-degrees of vibrational freedom using a heterodyne speckle imaging sensor system, said heterodyne speckle imaging sensor system comprising:
   a laser source emitting a linearly polarized laser,
   a first beam splitter to divide the linearly polarized laser from the laser source into a probe beam along a probe path and a reference beam along a reference path,
   a bi-convex probe lens in the probe path to provide focus adjustment for the probe beam,
   a first mirror in the probe path to reflect the probe beam as a redirected probe beam,
   a scattering source having a diffuse surface to scatter the redirected probe beam as a scattered radiation,
   bi-convex collecting lens to collect a portion of the scattered radiation as a collected radiation,
   a second mirror for redirecting the collected radiation as a propagated beam,
   plano-convex defocusing lens to defocus a field of the propagated beam,
   a third mirror to redirect the resulting defocused propagated beam,
   a polarizing filter to absorb horizontally polarized components of said propagating beam as a probe electric field towards an image plane,
   an arrangement of acousto-optic modulators to effect frequency offset of the electromagnetic field associated with the reference beam to result in a frequency offset reference beam,
   a reference mirror to redirect said frequency offset reference beam,
   a plano-convex reference lens to focus said redirected frequency offset reference beam as a focused reference beam,
   a reference spatial filter to spatial filter said focused reference beam to result in a diverging beam,
   a plano-convex collimating lens to collimate said diverging beam as a collimated reference beam,
   another polarizing filter to absorb horizontally polarized components of said collimated reference beam as a reference electric field towards said image plane,
   a second beam splitter to additively combine the probe and reference electric fields towards said image plane,
   a focal plane array disposed along said image plane, wherein said probe and reference electric fields as additively combined are sensed to output charges,
   a trans-impedance amplifier circuit to convert said charges into digital representations of temporal spatial irradiance data, and
   a computer to store a complete measurement of said temporal spatial irradiance data as pixel frames of image data and process the signal processing method for computing three-degrees of vibrational freedom;
   the signal processing method comprising the steps of:
   accessing said pixel frames of image data stored on the computer;
   high-pass filtering on the computer each pixel independently to isolate heterodyne signal from the complete measurement to output heterodyne information at a local oscillator frequency $\omega_{LO}$;
   applying a computation process for sequential estimates of a detected probe speckle pattern amplitude to compute on the computer two dimensions of tilt based on time sequences;
   applying a parallel demodulation process based on an arctangent demodulation for Doppler shifted heterodyne signals applied to each pixel to calculate on the computer z-axis velocity; and
   displaying a representation of the computed tilt based on time sequences and the calculated z-axis velocity on the computer.

2. The signal processing method according to claim 1, wherein said computation process for sequential estimates of a detected probe speckle pattern amplitude comprises the steps of:
   applying a temporal Hilbert transform to extract an envelope $2R|P|$ at each pixel and output a speckle pattern that shifts spatially for each subsequent frame;
   cross-correlating each frame with its prior time frame producing a sequence of new data frames each containing a spatial peak;
   estimating a peak position based on a center of a frame using a two dimensional parabolic spatial fit on a cross correlation frame to output a temporal sequence of peak locations applied in two dimensions; and
   converting the spatial shifts to units of object tilt difference $\Delta\theta$ and $\Delta\phi$ between subsequent image frames.

3. The signal processing method according to claim 2, wherein said temporal sequence of peak locations applied in two dimensions are based on two temporal frames with spatial shifts between subsequent image frames.

4. The signal processing method according to claim 2, wherein said units of object tilt difference are characterized by $\Delta\theta$ and $\Delta\phi$, wherein $\Delta\theta=s_x/2z$ and $\Delta\phi=s_y/2z$.

5. The signal processing method according to claim 1, wherein said parallel demodulation process based on an arctangent demodulation for Doppler shifted heterodyne signals applied to each pixel comprises the steps of:
   multiplying each pixel of said heterodyne information output by sine and cosine functions of the local oscillator frequency $\omega_{LO}$ to result in in-phase and quadrature time sequences;
   low pass filtering the in-phase and quadrature time sequences to remove unwanted components at frequencies greater than $\omega_{LO}$ to produce in-phase and quadrature low pass filter outputs;
   processing said in-phase and quadrature low pass filter outputs to yield an estimate of a Doppler phase at each pixel;
   estimating a velocity for each pixel using the Doppler phase;
   removing low signal strength pixels; and
   averaging the remaining pixels to reduce noise to output a velocity time series representing axial velocity in the z direction.

6. The signal processing method according to claim 5, wherein constructive interference from the diffuse scattering source produces some high amplitude field strengths from the probe that are accurately captured, and wherein the velocity estimates associated with high amplitude pixels produce accurate estimates of velocity.

7. The signal processing method according to claim 5, wherein said multiplying each pixel of said heterodyne information output by sine and cosine functions of the local oscillator frequency $\omega_{LO}$ results in in-phase $I_{demod}$ and quadrature $Q_{demod}$ time sequences.

8. The signal processing method according to claim 7, wherein said low pass filtering the in-phase and quadrature time sequences removes unwanted components at frequencies greater than $\omega_{LO}$, as follows:

$$Q_{demod}(t)=LP[HP[I(t)]\sin(\omega_{LO}t)]$$

$$I_{demod}(t)=LP[HP[I(t)]\cos(\omega_{LO}t)].$$

9. The signal processing method according to claim 8, wherein said processing of in-phase and quadrature low pass filter yields an estimate of a Doppler phase ψ at each pixel, wherein $$\psi \approx \mathrm{unwrap}\left[\tan^{-1}\left(\frac{Q_{demod}(t)}{I_{demod}(t)}\right)\right].$$

10. The signal processing method according to claim 9, wherein said estimating a velocity for each pixel using the Doppler phase is based on the relationship, $$v=\frac{\lambda}{4\pi}\left(\frac{\psi_2-\psi_1}{t_2-t_1}\right),$$

wherein v is the velocity.

* * * * *